(12) United States Patent
Takekoshi et al.

(10) Patent No.: US 6,497,889 B2
(45) Date of Patent: Dec. 24, 2002

(54) COSMETICS

(75) Inventors: Yoichiro Takekoshi, Rye, NY (US); Tomoya Takahashi, Tsuchiura; Toshio Oonuma, Tokyo, both of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/874,252

(22) Filed: Jun. 6, 2001

(65) Prior Publication Data

US 2002/0009472 A1 Jan. 24, 2002

(30) Foreign Application Priority Data

Jun. 20, 2000 (JP) .......................... 2000-183937

(51) Int. Cl.⁷ .............................. A61K 7/00; A61K 7/42
(52) U.S. Cl. ........................... 424/401; 424/59; 424/60; 424/400
(58) Field of Search ........................... 424/59, 60, 400, 424/401

(56) References Cited

U.S. PATENT DOCUMENTS 5,725,844 A * 3/1998 Gers-Barlag et al. .......... 424/59
6,037,481 A * 3/2000 Zuchetti et al. ............. 549/315

FOREIGN PATENT DOCUMENTS

| JP | 1-131107 | 5/1989 |
| JP | 5-339140 | 12/1993 |
| JP | 9-87126 | 3/1997 |
| JP | 11-139951 | 5/1999 |

* cited by examiner

*Primary Examiner*—Shelley A. Dodson
(74) *Attorney, Agent, or Firm*—Fitzpatrick, Cella, Harper & Scinto

(57) ABSTRACT

The present invention provides cosmetics comprising (1) hydroxyproline, an N-acylated hydroxyproline derivative or a salt thereof and (2) at least one component selected from the group consisting of water-soluble vitamins, oil-soluble vitamins, high molecular peptides, high molecular polysaccharides, sphingolipids and seaweed extracts.

28 Claims, No Drawings

COSMETICS

BACKGROUND OF THE INVENTION

The present invention relates to cosmetics having the activities to inhibit the skin aging and to improve the skin, in addition to the moisturizing function.

So far, aging-preventing materials have been widely employed in cosmetics for the purpose of obtaining cosmetic effects such as prevention of the skin aging and the skin deterioration which cause skin troubles such as wrinkles, sags and dry skin.

The aging-preventing materials employed in cosmetics are broadly classified into peroxide lipid inhibitors and cell activators.

Examples of the materials having the activity to inhibit peroxide lipid are α-hydroxy acid, vitamin A, β-carotene, vitamin $B_{12}$, vitamin E, pigments such as dimethylaminostyryl heptyl methyl thiazolium iodide and platonin, scutellaria root, rutin, sesame extract and tea extract. As the cell activators, Quaternium-45, glycolic acid, γ-amino acid, sialic acid, royal jelly, extract of *Swertia japonica* (Schult.) Makino, Japanese chirata, ginseng extract, etc. are known.

Known cell activators also include materials which promote collagen synthesis and materials having the activity to improve the skin.

Examples of the materials which promote collagen synthesis include ascorbic acid, various growth factors such as transforming growth factor β1, platelet-derived growth factor, fibroblast growth factor and insulin-like growth factor 1, and silk protein.

Examples of the materials having the activity to improve the skin include allantoin, aloe extract, ginseng extract, placenta extract, bovine blood freed of protein, and fermentation metabolites.

There is a report that hydroxyproline derivatives can be used as components of cosmetics to keep the skin elasticity by their activity to increase the oxygen consumption of disrupted mouse liver (Japanese Published Unexamined Patent Application No. 131107/89). However, the report contains neither description of the relationship between the increase in oxygen consumption of disrupted mouse liver and the effect on the human skin nor data concerning the effectiveness of compounds as components of cosmetics. Accordingly, it is not possible to conclude from the report that the hydroxyproline derivatives are effective as components of cosmetics. There has been no report that a significant improving effect on the skin can be obtained by using hydroxyproline or a derivative thereof in combination with a water-soluble vitamin, an oil-soluble vitamin, a high molecular peptide, a high molecular polysaccharide, a sphingolipid or a seaweed extract.

There are reports on cosmetics comprising mucin (Japanese Published Unexamined Patent Application No. 339140/93) or glycine betaine and pyrrolidone carboxylic acid or its salt (Japanese Published Unexamined Patent Application No. 87126/97) in combination with amino acids aimed at enhancing the moisturizing effect. There is also a report on a cosmetic comprising one or more components selected from the group consisting of glycyrrhetinic acid, a derivative thereof, glycyrrhizic acid and a salt thereof in combination with proline, etc. aimed at improving rough skin (Japanese Published Unexamined Patent Application No. 139951/99). In the reports, hydroxyproline is mentioned as one of the examples of amino acids and proline derivatives, but no data is given concerning the effect of a cosmetic comprising hydroxyproline in combination with a water-soluble vitamin, an oil-soluble vitamin, a high molecular peptide, a high molecular polysaccharide, a sphingolipid or a seaweed extract.

An object of the present invention is to provide a cosmetic having the activities to inhibit the skin aging and to improve the skin, in addition to the moisturizing function.

SUMMARY OF THE INVENTION

The present invention relates to cosmetics comprising (1) hydroxyproline, an N-acylated hydroxyproline derivative or a salt thereof and (2) at least one component selected from the group consisting of water-soluble vitamins, oil-soluble vitamins, high molecular peptides, high molecular polysaccharides, sphingolipids and seaweed extracts.

DETAILED DESCRIPTION OF THE INVENTION

Hydroxyproline widely occurs in nature as a major amino acid component of collagen and as an amino acid component of elastin. It is known that there exist eight kinds of stereoisomers of natural hydroxyproline, which are distinct in the following points: proline is the D-form or the L-form, the hydroxyl group is at the 3-position or the 4-position, and the stereoisomer is the cis-form or the trans-form.

Usually, trans-4-hydroxy-L-proline is common, but the presence of the other stereoisomers are extremely limited in nature.

Hydroxyproline can be obtained by subjecting collagen derived from animals such as pig and cow to acid hydrolysis and then purifying the hydrolysis product according to a conventional method. In obtaining hydroxyproline from such natural materials, it is necessary to be very careful about contamination with animal-derived viruses, prion, which is a causative protein of bovine spongiform encephalopathy, etc.

In the present invention, any hydroxyproline obtained by the above method can be used. However, hydroxyproline produced using microorganisms, which does not contain contaminants such as animal-derived viruses and prion, is preferably used.

Useful microorganisms include microorganisms carrying a proline 3-hydroxylase gene or a proline 4-hydroxylase gene derived from a microorganism belonging to a genus selected from the group consisting of the genera Amycolatopsis, Dactylosporangium and Streptomyces. Introduction of a proline 3-hydroxylase gene or a proline 4-hydroxylase gene derived from a microorganism belonging to a genus selected from the group consisting of the genera Amycolatopsis, Dactylosporangium and Streptomyces into a microorganism can be carried out according to the methods described in Molecular Cloning, A Laboratory Manual, Second Edition, Cold Spring Harbor Laboratory Press (1989), Current Protocols in Molecular Biology, John Wiley & Sons (1987–1997), etc.

Further, trans-4-hydroxy-L-proline can be produced using proline 4-hydroxylase isolated from a microorganism of the genus Amycolatopsis or Dactylosporangium (Japanese Published Unexamined Patent Application No. 313179/95), and cis-3-hydroxy-L-proline can be produced using proline 3-hydroxylase isolated from a microorganism of the genus Streptomyces (Japanese Published Unexamined Patent Application No. 322885/95) [Bioindustry, 14, 31 (1997)].

The acyl moiety of the N-acylated hydroxyproline derivatives used in the present invention includes straight-chain or branched acyl groups having 2–23 carbon atoms, for example, acetyl, propionyl, butyryl, isobutyryl, valeryl, hexanoyl, heptanoyl, octanoyl, decanoyl, eicosanoyl and lauroyl. Preferred are acetyl and propionyl.

The N-acylated hydroxyproline derivatives can be produced according to a known method.

That is, the N-acylated hydroxyproline derivatives can be prepared by N-acylating hydroxyproline in an aqueous medium or an organic solvent by the use of an active derivative (acid anhydride, acid chloride, etc.) of a fatty acid having an alkyl group having preferably 1–22 carbon atoms.

The obtained N-acylated hydroxyproline derivatives can be purified by conventional methods of purification such as crystallization and chromatography.

Examples of the salts of hydroxyproline or N-acylated hydroxyproline derivatives include alkali metal salts such as sodium salt and potassium salt, alkaline earth metal salts such as magnesium salt and calcium salt, ammonium salts such as ammonium salt and tetramethylammonium salt, and organic amine addition salts such as salts with morpholine and piperidine.

In the cosmetics of the present invention, hydroxyproline such as cis/trans-4-hydroxy-L/D-proline or cis/trans-3-hydroxy-L/D-proline, the N-acylated hydroxyproline derivatives or the salts thereof can be used alone or as a mixture.

The content of hydroxyproline, the N-acylated hydroxyproline derivatives or the salts thereof in the cosmetics may vary in a wide range according to the desired effect.

The cosmetics of the present invention are formulated to contain hydroxyproline, the N-acylated hydroxyproline derivatives or the salts thereof preferably in an amount of 0.01–5 wt %, more preferably 0.1–5 wt %, most preferably 0.5–3 wt % based on the total weight.

As the water-soluble vitamin, any cosmetically acceptable water-soluble vitamins may be employed. Examples of preferred water-soluble vitamins are vitamin $B_1$, vitamin $B_2$, vitamin $B_6$, pyridoxine, pyridoxine hydrochloride, vitamin $B_{12}$, pantothenic acid, nicotinic acid, nicotinamide, folic acid, vitamin C and vitamin H. Also useful are their salts (e.g., thiamine hydrochloride and sodium ascorbate) and derivatives (e.g., ascorbic acid-2-phosphate sodium salt and ascorbic acid-2-phosphate magnesium salt). The water-soluble vitamins can be obtained by conventional methods such as conversion by a microorganism, purification from a culture of a microorganism, the enzymatic method and chemical synthesis.

As the oil-soluble vitamin, any cosmetically acceptable oil-soluble vitamins may be employed. Examples of preferred oil-soluble vitamins are vitamin A, carotene, vitamin $D_2$, vitamin $D_3$ and vitamin E (e.g., dl-$\alpha$-tocopherol, d-$\alpha$-tocopherol and d-$\delta$-tocopherol). Also useful are their derivatives (e.g., ascorbyl palmitate, ascorbyl stearate, ascorbyl dipalmitate, dl-$\alpha$-tocopherol acetate, dl-$\alpha$-tocopherol nicotinate vitamin E, DL-pantothenyl alcohol, D-pantothenyl alcohol and pantothenyl ethyl ether). The oil-soluble vitamins can be obtained by conventional methods such as conversion by a microorganism, purification from a culture of a microorganism, the enzymatic method and chemical synthesis.

As the high molecular peptide, any cosmetically acceptable high molecular peptides may be employed. Examples of preferred high molecular peptides are collagen, hydrolyzed collagen, gelatin, elastin, hydrolyzed elastin and keratin. The high molecular peptides can be obtained by conventional methods such as purification from a culture of a microorganism, the enzymatic method and chemical synthesis. The high molecular peptides can be obtained usually by purification from natural materials such as the dermis of pig, cow, etc. and silk fibers of silkworm.

As the high molecular polysaccharide, any cosmetically acceptable high molecular polysaccharides may be employed. Examples of preferred high molecular polysaccharides are hydroxyethyl cellulose, xanthane gum, sodium hyaluronate, chondroitin sulfate and its salts (e.g., sodium salt). Chondroitin sulfate, its salts, etc. can be obtained usually by purification from mammals or fish.

As the sphingolipid, any cosmetically acceptable sphingolipids may be employed. Examples of preferred sphingolipids are ceramide, phytosphingosine and sphingoglycolipid. The sphingolipids can be obtained usually by purification from mammals, fish, shellfish, yeast, plants, etc. according to conventional methods or by chemical synthesis.

As the seaweed extract, any cosmetically acceptable seaweed extracts may be employed. Examples of preferred seaweed extracts are brown alga extract, red alga extract and green alga extract. Also useful are carrageenan, alginic acid, sodium alginate and potassium alginate obtained by purification from these seaweed extracts. The seaweed extracts can be obtained by purification from seaweed by conventional methods.

The components selected from the group consisting of water-soluble vitamins, oil-soluble vitamins, high molecular peptides, high molecular polysaccharides, sphingolipids and seaweed extracts are contained in the cosmetics of the present invention preferably in an amount of 0.0001–10 wt %, more preferably 0.005–5 wt %, most preferably 0.01–3 wt % based on the total weight.

The cosmetics of the present invention may be formulated to contain other components usually employed in cosmetics, as may be required, in addition to the above essential components.

The additional cosmetically acceptable components include fat and oil components, moisturizers, emollients, surfactants, organic and inorganic pigments, organic powders, ultraviolet absorbents, preservatives, disinfectants, antioxidants, plant extracts, pH regulators, alcohols, pigments, perfumes, blood-circulation promoters, refrigerants, antiperspirants and purified water.

The fat and oil components include ester fats and oils, hydrocarbon fats and oils, silicone fats and oils, fluorine fats and oils, and animal and plant fats and oils.

Examples of the ester fats and oils include esters such as glyceryl tri(2-ethylhexanoate), cetyl 2-ethylhexanoate, isopropyl myristate, butyl myristate, isopropyl palmitate, ethyl stearate, octyl palmitate, isocetyl isostearate, butyl stearate, ethyl linoleate, isopropyl linoleate, ethyl oleate, isocetyl myristate, isostearyl myristate, isostearyl palmitate, octyldodecyl myristate, diethyl sebacate, diisopropyl adipate, isoalkyl neopentanoate, glyceryl tri(capryl-caprinate), trimethylol propane tri(2-ethylhexanoate), trimethylol propane triisostearate, pentaerythritol tetra(2-ethylhexaonate), cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprinate, propylene glycol di(capryl-caprinate), propylene glycol dicaprylate, neopentyl glycol dicaprinate, neopentyl glycol dioctanoate, glyceryl tricaprylate, glyceryl triundecanoate, glyceryl triisopalmitate, glyceryl triisostearate, octyldodecyl neopentanoate, isostearyl octanoate, octyl isononanoate, hexyldecyl neodecanoate, octyldodecyl neodecanoate, isostearyl isostearate, octyldecyl isostearate, polyglycerol oleic acid ester, polyglycerol isostearic acid ester, triisocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di(2-ethylhexyl) succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate and isostearyl 12-stearoylhydroxystearate.

Examples of the hydrocarbon fats and oils are squalane, liquid paraffin, α-olefin oligomer, isoparaffin, ceresin, paraffin, liquid isoparaffin, polybutene, microcrystalline wax and vaseline.

Examples of the silicone fats and oils are polymethylsilicone, methylphenylsilicone, methylcyclopolysiloxane, octamethylpolysiloxane, decamethylpolysiloxane, dodecamethylcyclosiloxane, dimethylsiloxane-methylcetyloxysiloxane copolymers, dimethylsiloxane-methylstearoxysiloxane copolymers, alkyl-denatured silicone oil and amino-denatured silicone oil.

An example of the fluorine fats and oils is perfluoropolyether.

Examples of the animal and plant fats and oils are avocado oil, almond oil, olive oil, sesame oil, rice bran oil, safflower oil, soybean oil, corn oil, rapeseed oil, apricot kernel oil, palm kernel oil, palm oil, castor oil, sunflower oil, grape seed oil, cottonseed oil, coconut oil, kukui nut oil, wheat germ oil, rice germ oil, shea butter, evening primrose oil, macadamia nut oil, meadowfoam seed oil, egg yolk oil, beef tallow, horse oil, mink oil, orange roughy oil, jojoba oil, candelilla wax, carnauba wax, liquid lanolin and hardened castor oil.

The moisturizers include water-soluble low molecular moisturizers, fat-soluble low molecular moisturizers, water-soluble high molecular moisturizers and fat-soluble high molecular moisturizers.

Examples of the water-soluble low molecular moisturizers are serine, glutamine, sorbitol, mannitol, pyrrolidone-sodium carboxylate, glycerin, propylene glycol, 1,3-butylene glycol, ethylene glycol, polyethylene glycol (polymerization degree n=2 or more), polypropylene glycol (polymerization degree n=2 or more), polyglycerin (polymerization degree n=2 or more), lactic acid and lactate.

Examples of the fat-soluble low molecular moisturizers are cholesterol and cholesterol ester.

Examples of the water-soluble high molecular moisturizers are carboxyvinyl polymers, polyaspartate, tragacanth, xanthane gum, methyl cellulose, hydroxymethyl cellulose, hydroxyethyl cellulose, hydroxypropyl cellulose, carboxymethyl cellulose, water-soluble chitin, chitosan and dextrin.

Examples of the fat-soluble high molecular moisturizers are polyvinylpyrrolidone-eicosene copolymers, polyvinylpyrrolidone-hexadecene copolymers, nitrocellulose, dextrin fatty acid ester and high molecular silicone.

Examples of the emollients are long-chain acylglutamate cholesteryl ester, cholesteryl hydroxystearate, 12-hydroxystearic acid, stearic acid, rhodinic acid and lanolin fatty acid cholesteryl ester.

The surfactants include nonionic surfactants, anionic surfactants, cationic surfactants and amphoteric surfactants.

Examples of the nonionic surfactants are auto-emulsified glycerin monostearate, propylene glycol fatty acid ester, glycerin fatty acid ester, polyglycerin fatty acid ester, sorbitan fatty acid ester, POE (polyoxyethylene) sorbitan fatty acid ester, POE sorbitol fatty acid ester, POE glycerin fatty acid ester, POE alkyl ether, POE fatty acid ester, POE hardened castor oil, POE castor oil, POE-POP (polyoxyethylene-polyoxypropylene) copolymers, POE-POP alkyl ether, polyether-denatured silicone, alkanolamide laurate, alkylamine oxide and hydrogenated soybean phospholipid.

Examples of the anionic surfactants are fatty acid soap, α-acylsulfonate, alkylsulfonate, alkylallylsulfonate, alkylnaphthalenesulfonate, alkyl sulfate, POE alkyl ether sulfate, alkylamide sulfate, alkyl phosphate, POE alkyl phosphate, alkylamide phosphate, alkyloylalkyltaurine salt, N-acylamino acid salt, POE alkyl ether carboxylate, alkylsulfosuccinate, sodium alkylsulfoacetate, acylated hydrolyzed collagen peptide salt and perfluoroalkyl phosphoric acid ester.

Examples of the cationic surfactants are alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, diethylaminoethyl-stearamide, dimethylaminopropyl-stearamide and lanolin derivative quaternary ammonium salt.

Suitable amphoteric surfactants are those of the following types: carboxybetaine, amidobetaine, sulfobetaine, hydroxysulfobetaine, amidosulfobetaine, phosphobetaine, aminocarboxylate, imidazoline derivative and amidoamine.

The organic and inorganic pigments include inorganic pigments such as silicic acid, silicic acid anhydride, magnesium silicate, talc, sericite, mica, kaolin, iron oxide red, clay, bentonite, titanium-coated mica, bismuth oxychloride, zirconium oxide, magnesium oxide, zinc oxide, titanium oxide, aluminium oxide, calcium sulfate, barium sulfate, magnesium sulfate, calcium carbonate, magnesium carbonate, iron oxide, ultramarine blue, chromium oxide, chromium hydroxide, carmine, carbon black, and complexes thereof; organic pigments such as polyamide, polyester, polypropylene, polystyrene, polyurethane, vinyl resin, urea resin, phenol resin, fluororesin, silicone resin, acrylic resin, melamine resin, epoxy resin, polycarbonate resin, divinyl benzene-styrene copolymer, silk powder, cellulose, CI pigment yellow and CI pigment orange; and complexes of these inorganic pigments and organic pigments.

Examples of the organic powders are metal soaps such as calcium stearate; alkylphosphoric acid polyvalent metal salts such as sodium zinc cetylphosphate, zinc laurylphosphate and calcium laurylphosphate; acylamino acid polyvalent metal salts such as N-lauroyl-β-alanine calcium salt, N-lauroyl-β-alanine zinc salt and N-lauroylglycine calcium salt; amidosulfonic acid polyvalent metal salts such as N-lauroyl-taurine calcium salt and N-palmitoyl-taurine calcium salt; N-acyl basic amino acids such as Nε-lauroyl-L-lysine, Nε-palmitoyllysine, Nα-palmitoylornithine, Nα-lauroylarginine and Nα-hardened beef tallow fatty acid acylarginine; N-acylpolypeptides such as N-lauroylglycylglycine; α-amino fatty acids such as α-aminocaprylic acid and α-aminolauric acid; polyethylene, polypropylene, nylon, polymethyl methacrylate, polystyrene, divinyl benzene-styrene copolymer and ethylene tetrafluoride.

Examples of the ultraviolet absorbents are para-aminobenzoic acid, ethyl para-aminobenzoate, amyl para-aminobenzoate, octyl para-aminobenzoate, ethylene glycol salicylate, phenyl salicylate, octyl salicylate, benzyl salicylate, butylphenyl salicylate, homomenthyl salicylate, benzyl cinnamate, 2-ethoxyethyl para-methoxycinnamate, octyl para-methoxycinnamate, glyceryl mono(2-ethylhexanoate) dipara-methoxycinnamate, isopropyl para-methoxycinnamate, diisopropyl-diisopropylcinnamic acid ester mixtures, urocanic acid, ethyl urocanate, hydroxymethoxybenzophenone, hydroxymethoxybenzophenonesulfonic acid and salts thereof, dihydroxymethoxybenzophenone, sodium dihydroxymethoxybenzophenonedisulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, and 2-(2-hydroxy-5-methylphenyl)benzotriazole.

Examples of the preservatives are methylparaben and propylparaben.

Examples of the disinfectants are hinokitiol, triclosan, trichlorohydroxydiphenyl ether, chlorhexidine gluconate, phenoxyethanol, resorcin, isopropylmethylphenol, azulene, salicylic acid, zinc pyrithione, benzalkonium chloride, photosensitizing dye No. 301, sodium mononitroguaiacol and undecylenic acid.

Examples of the antioxidants are butylhydroxyanisole, propyl gallate and erythorbic acid.

Examples of the plant extracts are extract of *Angelica keiskei* (Miq.)Koidz., avocado extract, extract of *Hydrangea macrophylla* (Thunb.) Ser. subsp. *serrata* (Thunb.) *Makino* var. *thunbergii* (Sieb.)Makino, althaea extract, arnica extract, aloe extract, apricot extract, apricot kernel extract, gingko extract, fennel extract, turmeric extract, oolong tea extract, extract of fruits of memorial rose, Echinacea leaf extract, extract of scutellaria root, extract of Phellodendron bark, extract of Japanese coptis, barley extract, extract of *Hypericum erectrum* Thunb., extract of *Lamium album* var. *barbatum* (Sieb. et Zucc.) Franch. et Savat, watercress extract, orange extract, chamomile extract, carrot extract, extract of *Artemisia capillaris* Thunb., licorice extract, hibiscus flower extract, extract of *Pyracantha fortuneana*, kiwi fruit extract, cinchona extract, cucumber extract, extract of *Gardenia jasminoides* Ellis forma *grandiflora* (Lour.) Makino, extract of *Sasa veitchii* (Carr.) Rehd., extract of *Sophora flavescens* Aiton, walnut extract, grapefruit extract, clematis extract, chlorella extract, mulberry extract, gentian extract, black tea extract, common confrey extract, collagen, cowberry extract, extract of *Asarum sieboldii* Miq., bupleurum extract, salvia extract, soapwort extract, bamboo grass extract, crataegus extract, zanthoxylum extract, shiitake mushroom extract, extract of Rehmannia root, extract of lithospermum root, perilla extract, extract of *Tilia japonica* (Miq.) Simonkai, meadowsweet extract, peony extract, extract of calamus root, white birch extract, extract of *Equisetum arvense* L., extract of *Hedera helix* L., English hawthorn extract, European elder extract, yarrow extract, peppermint extract, sage extract, tree mallow extract, cnidium extract, extract of *Swertia japonica* (Schult.) Makino, soybean extract, extract of fruits of common jujube, thyme extract, tea extract, clove extract, cogon extract, extract of dried orange peel, ligusticum extract, common marigold extract, peach kernel extract, bitter orange peel extract, extract of *Houttuynia cordata* Thunb., tomato extract, ginseng extract, garlic extract, wild rose extract, hibiscus extract, extract of roots of *Ophiopogon japonicus* (L. f.) Ker. Gawl., parsley extract, honey, hamamelis extract, Parietaria extract, extract of *Isodon japonicus* (Burm.) Hara, bisabolol, loquat extract, coltsfoot extract, butterbur flower extract, tuckahoe extract, butcher's-broom extract, grape extract, propolis, luffa extract, safflower extract, extract of big leaf European linden, tree peony extract, hop extract, pine extract, horse chestnut extract, extract of *Lysichiton camtschatcense* (L.) Schott, extract of *Sapindus mukurossi* Gaertn., Melissa extract, peach extract, bluebottle extract, eucalyptus extract, extract of *Saxifraga stolonifera* Meerb., extract of *Citrus junos* Sieb. ex Miq., coix seed extract, mugwort extract, lavender extract, apple extract, lettuce extract, lemon extract, Chinese milk vetch extract, rose extract, rosemary extract and Roman chamomile extract.

Examples of the pH regulators are citric acid, sodium citrate, malic acid, sodium malate, fumaric acid, sodium fumarate, succinic acid, sodium succinate, sodium hydroxide and disodium hydrogenphosphate.

The alcohols include higher alcohols such as cetyl alcohol.

The additional components mentioned above are merely illustrative, and not limitative. Any of the above components can be employed in such range that the object and the effect of the present invention are not impaired. The suitable content thereof is preferably 0.01–5 wt %, more preferably 0.01–3 wt % based on the total weight.

The cosmetics of the present invention may take the forms of solution, emulsion, paste mixture, etc.

There is no specific restriction as to the form of cosmetics as products and suitable examples are emulsion, cream, lotion, pack, foundation, enriched lotion and hair-care cosmetic.

Specific examples of the cosmetics of the present invention are facial washing cream, facial washing foam, cleansing cream, cleansing milk, cleansing lotion, massage cream, cold cream, moisturizing cream, emulsion, lotion, pack, after-shaving cream, sun-screening cream, suntan oil, body shampoo, hair shampoo, hair rinse, hair conditioner, hair-nourishing agent, hair-growing agent, stick pomade, hair cream, hair liquid, hair-setting lotion, hair spray, hair dye, hair bleach, coloring rinse, coloring spray, permanent wave liquid, pressed powder, loose powder, eye shadow, hand cream and lipstick.

The cosmetics of the present invention can be prepared from hydroxyproline, the N-acylated hydroxyproline derivatives or the salts thereof, and the components selected from the group consisting of water-soluble vitamins, oil-soluble vitamins, high molecular peptides, high molecular polysaccharides, sphingolipids and seaweed extracts (and if necessary, the additional components described above) according to known methods, for example, the method described in Mitsuo Matsumoto ed., "Development Manual of Preparations for Percutaneous Application" 1st ed., Seishi Shoin (1985).

The cosmetics of the present invention improve the moisturization of the skin, rough skin, wrinkles, and elasticity and tautness of the skin, and are effective for preventing the skin aging and improving the skin.

Example 1 Preparation of a Cream

A cream having the following composition (% means wt %) was prepared.

| Ingredient | Amount |
|---|---|
| Polyethylene glycol monostearate (PEG 55 Nikkou Chemical Co., Ltd.) | 2.00 (%) |
| Auto-emulsified glycerin monostearate | 5.00 |
| Cetyl alcohol | 4.00 |
| Squalane | 6.00 |
| Glyceryl tri (2-ethylhexanoate) | 6.00 |
| 1,3-Butylene glycol | 7.00 |
| L-Ascorbic acid-2-phosphate magnesium salt | 3.00 |
| Trans-4-hydroxy-L-proline | 1.00 |

Purified water was added to make up to 100%.

Example 2 Preparation of a Lotion

A lotion having the following composition (% means wt %) was prepared.

| Ingredient | Amount |
|---|---|
| Trans-4-hydroxy-L-proline | 3.00 (%) |
| L-Ascorbic acid-2-phosphate magnesium salt | 1.00 |
| Water-soluble collagen (1% aqueous solution) | 1.00 |
| Sodium citrate | 0.10 |
| Citric acid | 0.05 |
| Licorice extract | 0.20 |
| 1,3-Butylene glycol | 3.00 |

Purified water was added to make up to 100%.

Example 3 Preparation of a Pack

A pack having the following composition (% means wt %) was prepared.

| Ingredient | Amount |
|---|---|
| Polyvinyl alcohol | 13.00 (%) |
| L-Ascorbic acid-2-phosphate magnesium salt | 1.00 |
| Trans-4-hydroxy-L-proline | 5.00 |
| Lauroyl hydroxyproline | 1.00 |
| Water-soluble collagen (1% aqueous solution) | 2.00 |
| 1,3-Butylene glycol | 3.00 |
| Ethanol | 5.00 |

Purified water was added to make up to 100%.

Example 4 Preparation of an Enriched Lotion

An enriched lotion having the following composition (% means wt %) was prepared.

| Ingredient | Amount |
|---|---|
| Hydroxyethyl cellulose (2% aqueous solution) | 12.00 (%) |
| Xanthane gum (2% aqueous solution) | 2.00 |
| Trans-4-hydroxy-L-proline | 2.00 |
| 1,3-Butylene glycol | 6.00 |
| Concentrated glycerin | 4.00 |
| Sodium hyaluronate (1% aqueous solution) | 5.00 |

Purified water was added to make up to 100%.

Example 5 Preparation of a Lipstick

A lipstick having the following composition (% means wt %) was prepared.

| Ingredient | Amount |
|---|---|
| Candelilla wax | 10.00 (%) |
| Carnauba wax | 8.00 |
| Microcrystalline wax | 3.00 |
| Liquid lanolin | 15.00 |
| Glyceryl tri (2-ethylhexanoate) | 20.00 |
| Hardened castor oil | 5.00 |
| Trans-4-hydroxy-L-proline | 2.00 |
| dl-α-Tocopherol acetate | 0.01 |

Castor oil was added to make up to 100%.

Example 6 Preparation of a Lotion

A lotion having the following composition (% means wt %) was prepared.

| Ingredient | Amount |
|---|---|
| N-Acetyl-trans-4-hydroxy-L-proline | 3.00 (%) |
| L-Ascorbic acid-2-phosphate magnesium salt | 1.00 |
| Brown alga extract | 1.00 |
| Sodium citrate | 0.10 |
| Citric acid | 0.05 |
| 1,3-Butylene glycol | 3.00 |

Purified water was added to make up to 100%.

Example 7 Preparation of a Cream

A cream having the following composition (% means wt %) was prepared.

| Ingredient | Amount |
|---|---|
| Polyethylene glycol monostearate | 2.00 (%) |
| Auto-emulsified glycerin monostearate | 5.00 |
| Cetyl alcohol | 4.00 |
| Squalane | 6.00 |
| Glyceryl tri (2-ethylhexanoate) | 6.00 |
| N-Acetyl-trans-4-hydroxy-L-proline | 1.00 |
| Sphingoglycolipid | 1.00 |
| 1,3-Butylene glycol | 7.00 |

Purified water was added to make up to 100%.

Example 8 Preparation of a Lotion

A lotion having the following composition (% means wt %) was prepared.

| Ingredient | Amount |
|---|---|
| N-Acetyl-trans-4-hydroxy-L-proline | 3.00 (%) |
| L-Ascorbic acid-2-phosphate magnesium salt | 1.00 |
| Water-soluble collagen (1% aqueous solution) | 1.00 |
| Sodium citrate | 0.10 |
| Citric acid | 0.05 |
| 1,3-Butylene glycol | 3.00 |

Purified water was added to make up to 100%.

Test Example 1

The cream prepared in Example 1 was applied to 20 subjects once a day for 28 days. To evaluate the moisturizing effect, the low frequency conductivity (=water content) of the skin was measured with SKICON-200 (IBS Co., Ltd.) by putting the probe vertically to the test part of skin. The low frequency conductivities measured before and after the application of the cream were compared. The evaluation results are shown in Table 1.

As a control group, a composition prepared from the ingredients shown in Example 1 excluding trans-4-hydroxy-L-proline and L-ascorbic acid-2-phosphate magnesium salt was applied to 20 subjects.

TABLE 1

| Moisturizing effect | Number of subjects | |
|---|---|---|
| | Control group | Test group |
| Enhanced | 3 | 11 |
| Somewhat enhanced | 5 | 4 |
| No change | 12 | 5 |

The evaluation standard in Table 1 is as follows (the same shall apply to Tables 3, 4, 6 and 8).

Moisturizing effect

Enhanced: 115% ≦ relative conductivity

Somewhat enhanced: 105% ≦ relative conductivity < 115%

No change: 105% > relative conductivity

The relative conductivity was calculated by the following equation:

Relative conductivity=Low frequency conductivity after application/Low frequency conductivity before application×100 (%)

As shown in Table 1, the cosmetic of the present invention was evaluated to be effective with 75% of the subjects and thus showed a high moisturizing effect.

Test Example 2

The lotion prepared in Example 2 was applied to 12 subjects once a day for 28 days, and the elasticity of the skin was evaluated using Cutometer (SEM474 COURAGEK-HAZAKA electronic GmbH). The evaluation results are shown in Table 2.

As a control group, a composition prepared from the ingredients shown in Example 2 excluding trans-4-hydroxy- L-proline, L-ascorbic acid-2-phosphate magnesium salt and water-soluble collagen was applied to 12 subjects.

TABLE 2

| Elasticity | Number of subjects | |
| --- | --- | --- |
| | Control group | Test group |
| Improved | 2 | 4 |
| Somewhat improved | 3 | 3 |
| No change | 7 | 5 |

The evaluation standard in Table 2 is as follows (the same shall apply to Table 7).
Elasticity
  Improved: 115%≦relative elasticity
  Somewhat improved: 105%≦relative elasticity<115%
  No change: 105%>relative elasticity
The relative elasticity was calculated by the following equation:

Relative elasticity=Elasticity after application/Elasticity before application×100 (%)

As shown in Table 2, the cosmetic of the present invention was evaluated to be effective with 58% of the subjects and thus showed a high inhibitory activity against the skin aging.

Test Example 3

The pack prepared in Example 3 was applied to 14 subjects for 20 minutes once a day for 28 days. To evaluate the moisturizing effect, the low frequency conductivity (=water content) of the skin was measured with SKICON-200 (IBS Co., Ltd.) by putting the probe vertically to the test part of skin. The low frequency conductivities measured before and after the application of the pack were compared. The evaluation results are shown in Table 3.

As a control group, a composition prepared from the ingredients shown in Example 3 excluding trans-4-hydroxy-L-proline, L-ascorbic acid-2-phosphate magnesium salt and lauroyl hydroxyproline was applied to 14 subjects.

TABLE 3

| Moisturizing effect | Number of subjects | |
| --- | --- | --- |
| | Control group | Test group |
| Enhanced | 2 | 9 |
| Somewhat enhanced | 3 | 4 |
| No change | 9 | 1 |

As shown in Table 3, the cosmetic of the present invention was evaluated to be effective with 93% of the subjects and thus showed a very high moisturizing effect.

Test Example 4

The enriched lotion prepared in Example 4 was applied to 14 subjects once a day for 28 days. To evaluate the moisturizing effect, the low frequency conductivity (=water content) of the skin was measured with SKICON-200 (IBS Co., Ltd.) by putting the probe vertically to the test part of skin. The low frequency conductivities measured before and after the application of the enriched lotion were compared. The evaluation results are shown in Table 4.

As a control group, a composition prepared from the ingredients shown in Example 4 excluding trans-4-hydroxy-L-proline, xanthane gum and sodium hyaluronate was applied to 14 subjects.

TABLE 4

| Moisturizing effect | Number of subjects | |
| --- | --- | --- |
| | Control group | Test group |
| Enhanced | 2 | 8 |
| Somewhat enhanced | 3 | 4 |
| No change | 9 | 2 |

As shown in Table 4, the cosmetic of the present invention was evaluated to be effective with 86% of the subjects and thus showed a very high moisturizing effect.

Test Example 5

The lipstick prepared in Example 5 was applied to 12 subjects once a day for 28 days. To evaluate the skin-improving effect, the appearance of the lips was observed and compared with that before the application of the lipstick. The evaluation results are shown in Table 5.

As a control group, a composition prepared from the ingredients shown in Example 5 excluding trans-4-hydroxy-L-proline and dl-α-tocopherol acetate was applied to 12 subjects.

TABLE 5

| Appearance | Number of subjects | |
| --- | --- | --- |
| | Control group | Test group |
| Smoothened | 2 | 6 |
| Somewhat smoothened | 3 | 4 |
| No change | 7 | 2 |

As shown in Table 5, the cosmetic of the present invention was evaluated to be effective with 83% of the subjects and thus showed a high improving effect on the skin.

Test Example 6

The lotion prepared in Example 6 was applied to 12 subjects once a day for 28 days. To evaluate the moisturizing effect, the low frequency conductivity (=water content) of the skin was measured with SKICON-200 (IBS Co., Ltd.) by putting the probe vertically to the test part of skin. The low frequency conductivities measured before and after the application of the lotion were compared. The evaluation results are shown in Table 6.

As a control group, a composition prepared from the ingredients shown in Example 6 excluding N-acetyl-trans-4-hydroxy-L-proline, brown alga extract and L-ascorbic acid -2-phosphate magnesium salt was applied to 12 subjects.

TABLE 6

| Moisturizing effect | Number of subjects | |
| --- | --- | --- |
| | Control group | Test group |
| Enhanced | 2 | 4 |
| Somewhat enhanced | 3 | 3 |
| No change | 7 | 5 |

As shown in Table 6, the cosmetic of the present invention was evaluated to be effective with 58% of the subjects and thus showed a high moisturizing effect.

Test Example 7

The cream prepared in Example 7 was applied to 20 subjects once a day for 28 days, and the elasticity of the skin was evaluated using Cutometer (SEM474 COURAGEK-HAZAKA electronic GmbH). The evaluation results are shown in Table 7.

As a control group, a composition prepared from the ingredients shown in Example 7 excluding sphingoglycolipid and N-acetyl-trans-4-hydroxy-L-proline was applied to 20 subjects.

TABLE 7

| Elasticity | Number of subjects | |
|---|---|---|
| | Control group | Test group |
| Improved | 3 | 11 |
| Somewhat improved | 5 | 4 |
| No change | 12 | 5 |

As shown in Table 7, the cosmetic of the present invention was evaluated to be effective with 75% of the subjects and thus showed a high inhibitory activity against the skin aging.

Test Example 8

The lotion prepared in Example 8 was applied to 12 subjects once a day for 28 days. To evaluate the moisturizing effect, the low frequency conductivity (water content) of the skin was measured with SKICON-200 (IBS Co., Ltd.) by putting the probe vertically to the test part of skin. The low frequency conductivities measured before and after the application of the lotion were compared. The evaluation results are shown in Table 8.

As a control group, a composition prepared from the ingredients shown in Example 8 excluding N-acetyl-trans-4-hydroxy-L-proline, L-ascorbic acid-2-phosphate magnesium salt and water-soluble collagen was applied to 12 subjects.

TABLE 8

| Moisturizing effect | Number of subjects | |
|---|---|---|
| | Control group | Test group |
| Enhanced | 2 | 4 |
| Somewhat enhanced | 3 | 3 |
| No change | 7 | 5 |

As shown in Table 8, the cosmetic of the present invention was evaluated to be effective with 58% of the subjects and thus showed a high moisturizing effect.

What is claimed is:

1. A cosmetic comprising (1) hydroxyproline, an N-acylated hydroxyproline derivative or a salt thereof and (2) at least one component selected from the group consisting of water-soluble vitamins, oil-soluble vitamins, high molecular peptides, high molecular polysaccharides, sphingolipids and seaweed extracts.

2. The cosmetic according to claim 1, wherein the amount of said hydroxyproline, N-acylated hydroxyproline derivative or salt thereof is 0.01–5 wt % based on the total weight.

3. The cosmetic according to claim 1, wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

4. The cosmetic according to claim 2, wherein said hydroxyproline is selected from the group consisting of cis-4-hydroxy-L-proline, cis-4-hydroxy-D-proline, cis-3-hydroxy-L-proline, cis-3-hydroxy-D-proline, trans-4-hydroxy-L-proline, trans-4-hydroxy-D-proline, trans-3-hydroxy-L-proline and trans-3-hydroxy-D-proline.

5. The cosmetic according to claim 1, wherein said hydroxyproline is hydroxyproline produced by using a microorganism.

6. The cosmetic according to claim 2, wherein said hydroxyproline is hydroxyproline produced by using a microorganism.

7. The cosmetic according to claim 3, wherein said hydroxyproline is hydroxyproline produced by using a microorganism.

8. The cosmetic according to claim 4, wherein said hydroxyproline is hydroxyproline produced by using a microorganism.

9. The cosmetic according to claim 5, wherein said microorganism carries an introduced proline 3-hydroxylase or proline 4-hydroxylase gene derived from a microorganism belonging to a genus selected from the group consisting of the genera Amycolatopsis, Dactylosporangium and Streptomyces.

10. The cosmetic according to claim 6, wherein said microorganism carries an introduced proline 3-hydroxylase or proline 4-hydroxylase gene derived from a microorganism belonging to a genus selected from the group consisting of the genera Amycolatopsis, Dactylosporangium and Streptomyces.

11. The cosmetic according to claim 7, wherein said microorganism carries an introduced proline 3-hydroxylase or proline 4-hydroxylase gene derived from a microorganism belonging to a genus selected from the group consisting of the genera Amycolatopsis, Dactylosporangium and Streptomyces.

12. The cosmetic according to claim 8, wherein said microorganism carries an introduced proline 3-hydroxylase or proline 4-hydroxylase gene derived from a microorganism belonging to a genus selected from the group consisting of the genera Amycolatopsis, Dactylosporangium and Streptomyces.

13. The cosmetic according to claim 1, wherein the acyl moiety of said N-acylated hydroxyproline derivative is an acyl group having 2–23 carbon atoms.

14. The cosmetic according to claim 2, wherein the acyl moiety of said N-acylated hydroxyproline derivative is an acyl group having 2–23 carbon atoms.

15. The cosmetic according to claim 1, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

16. The cosmetic according to claim 2, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

17. The cosmetic according to claim 3, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

18. The cosmetic according to claim 4, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

19. The cosmetic according to claim 5, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

20. The cosmetic according to claim 6, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

21. The cosmetic according to claim 7, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

22. The cosmetic according to claim 8, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

23. The cosmetic according to claim 9, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

24. The cosmetic according to claim 10, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

25. The cosmetic according to claim 11, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

26. The cosmetic according to claim 12, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

27. The cosmetic according to claim 13, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

28. The cosmetic according to claim 14, wherein the amount of said components selected from the group consisting of water-soluble vitamins, oil-soluble vitamins, high molecular peptides, high molecular polysaccharides, sphingolipids and seaweed extracts is 0.0001–10 wt % based on the total weight.

\* \* \* \* \*